United States Patent
Tricárico et al.

(10) Patent No.: US 6,750,051 B2
(45) Date of Patent: Jun. 15, 2004

(54) COMPOSITIONS AND METHODS FOR ENHANCING FIBER DIGESTION

(75) Inventors: Juan M. Tricárico, Lexington, KY (US); Karl A. Dawson, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/121,476

(22) Filed: Apr. 10, 2002

(65) Prior Publication Data

US 2003/0035822 A1 Feb. 20, 2003

Related U.S. Application Data

(60) Provisional application No. 60/282,822, filed on Apr. 10, 2001.

(51) Int. Cl.$^7$ .............................. C12N 9/00; C12N 1/00
(52) U.S. Cl. ....................................... 435/243; 435/183
(58) Field of Search ........................................... 435/183

(56) References Cited

U.S. PATENT DOCUMENTS

| | | | |
|---|---|---|---|
| 5,426,043 A | 6/1995 | De Graaff et al. | 435/197 |
| 5,720,971 A | 2/1998 | Beauchemin et al. | 424/438 |
| 5,763,260 A | 6/1998 | De Graaff et al. | 435/274 |
| 5,830,734 A | 11/1998 | Christgau et al. | 435/196 |
| 5,948,454 A | 9/1999 | Virkki et al. | 426/53 |
| 6,037,161 A | 3/2000 | Christgau et al. | 435/197 |
| 6,264,946 B1 | 7/2001 | Mullertz et al. | 424/94.2 |

FOREIGN PATENT DOCUMENTS

WO     WO 9636701     * 11/1996

OTHER PUBLICATIONS

Borneman et al., Appl. Microbiol. Biotechnol., 1990, 33, 345–51.*
Beauchemin, K.A. and Rode, L.M., "Use of feed enzymes in ruminant nutrition" in *Animal Science Research and Development, Meeting Future Changes*, L.M. Rode, (Ed), Minister of Supply and Services Canada, Ottawa, Canada, pps. 103–130.
Beauchemin, K.A. et al., "Use of Feed Enzymes in Ruminant Nutrition" in *Proceedings of the Pacific Northwest Nutrition Conference*, Vancouver, BC. pps. 121–135 (1998).
Biely, P. et al., "Cooperativity of Esterases and Xylanases in the Enzymatic Degradation of Acetyl Xylan"; *Biotechnology* (1986) 4:731–733.
Blum, D.L. et al., "Characterization of an Acetyl Xylan Esterase from the Anaerobic Fungus Orpinomyces sp. Strain PC–2"; (1999) *Applied and Environmental Microbiology* 65(9):3990–3995.
Chen, H. et al., "Biomass Degrading Enzymes from Anaerobic Rumen Fungi" (1995) *SASS Bulletin, Biochemistry and Biotechnology* 8:1–6.

Christov L.P. and Prior B.A., "Esterases of xylan–degrading microorganisms: Production, properties, and significance"; (1993) *Enzyme Microb. Technol.* 15:460–475.
Cybinski, D.H. et al., "An acetylxylan esterase and a xylanase expressed from genes cloned from the ruminal fungus *Neocallimastix patriciarum* act synergistically to degrade acetylated xylans"; (1999) *Appl. Microbiol. Biotechnol.* 52:221–225.
Dalrymple, B.P. et al., "Three *Neocallimastix patriciarum* esterases associated with the degradation of complex polysaccharides are members of a new family of hydrolases"; (1997) *Microbiology* 143:2605–2614.
Harper,E.G. et al., "The effect of *Aspergillus oryzae* fermentation extract on the anaerobic fungi *Neocallimastix frontalis* EB 188, *Piromyces communis* DC 193 and Orpinomysces ssp. RW 206: generalized effects and component analysis"; (1996) *Appl. Microbiol. Biotechnol.* 45:817–821.
Kung, Jr. L., "Enzymes for Lactating Dairy Cows: New Theories and Applications",; (2001) $12_{th}$ *Annual Florida Ruminant Nutrition Symposium*, pps. 29–43.
Lee, S.S. et al., "Influence of an anaerobic fungal culture administration on in vivo ruminal fermentation and nutrient digestion"; (Dec. 2000) *Animal Feed Science and Technology* 88:201–217.
Lee, S.S. et al., "Relative Contributions of Bacteria, Protozoa, and Fungi to In Vitro Degradation of Orchard Grass Cell Walls and Their Interactions"; (Sep. 2000) *Applied and Environmental Microbiology* 66(9):3807–3813.
Lewis, G.E. et al., "Effect of Direct–Fed Fibrolytic Enzymes on the Digestive Characteristics of a Forage–Based Diet Fed to Beef Steers"; (1996) *Journal of Animal Sciences* 74:1310–1321.
McDermid, Kevin P.et al., "Purification and Properties of an Acetylxylan Esterase from *Fibrobacter succinogenes* S85"; (1990) 56(12):3805–3810.
Morgavi, D.P. et al., "Synergy Between Ruminal Fibrolytic Enzymes and Enzymes from *Trichoderma Longibrachiatum*"; (2000) *J. of Dairy Science* 83(6):1310–1321.
Morgavi, D.P. et al., "Stability and stabilization of potential feed additive enzymes in rumen fluid"; (2000) *Enzyme and Microbial Technology* 26:171–177.

(List continued on next page.)

*Primary Examiner*—Michael Meller
(74) *Attorney, Agent, or Firm*—Greenlee Winner and Sullivan PC

(57) ABSTRACT

Methods and enzyme supplements for enhancing fiber digestion in mammals and birds are described. The supplement comprises an effective amount of acetyl esterase, formulated for feeding to animals consuming significant percentages of forages in the diet. The compositions of this invention improve dry matter and neutral detergent fiber disappearance rates, and are useful dietary supplements for improving fiber digestion. The compositions of this invention may be utilized alone or in combination with known exogenous fibrolytic enzyme supplement to improve fiber digestion in mammals and birds. The acetyl esterase advantageously used in the compositions and methods of the present invention is produced by a ruminal isolate of Orpinomyces.

13 Claims, 4 Drawing Sheets

OTHER PUBLICATIONS

Nsereko, V.L. et al., "Effects of fungal enzyme preparations on hydrolysis and subsequent degradation of alfalfa hay fiber by mixed rumen microorganisms in vitro"; (2000) *Animal Feed Science and Technology* 88:153–170.

Tricarico, J.M., Dawson, K.A., "Contribution of an acetyl esterase containing enzyme preparation to the action of exogenous enzyme supplements for ruminants"; (2001) *J. Anim. Sci.* (Abstract only).

Tricarico, J.M., Dawson,K.A., "Effects of an ecetyl esterase containing preparaion produced by a ruminal fungal isolate on in vitro ruminal fermentations"; (2001) *J. Anim. Sci.* (Abstract only).

Varel, V.H., et al. "In Vitro Stimulation of Forage Fiber Degradation by Ruminal Microorganisms and *Aspergillus oryzae* Fermentation Extract"; (1993) *Applied and Environmental Microbiology* 59(10):3171–3176.

Wang, G.J., "Effects of enzyme supplementation and irradiation of rice bran on th performance of Leghorn and broiler chicks"; (1997) *Enzymes in Poultry and Swine Nutrition* R.R. Marquardt and Z. Han, Eds. International Development Research Center, Ottawa, Canada.

Williamson, G. et al., "Hairy plant polysaccharides: a close shave with microbial esterases"; (1998) 144:2011–2023.

* cited by examiner

COMPOSITIONS AND METHODS FOR ENHANCING FIBER DIGESTION

CROSS REFERENCE TO RELATED APPLICATIONS

This application claims the benefit of U.S. Provisional Patent Application Ser. No. 60/282,822, filed Apr. 10, 2001.

BACKGROUND OF THE INVENTION

This invention relates to compositions containing acetyl esterases for enhancing digestion of fiber in animals, including mammals and birds, and to methods for improving nutrient digestion by supplementation, feeds, feed concentrates and mineral supplements with compositions comprising acetyl esterase, especially a composition derived from culturing a ruminal isolate of Orpinomyces, said isolate named Strain KY herein.

Supplementation of animal feed with exogenous enzymes for purposes of improvement of animal performance is known in the art. Such use is related to the central role of digestive enzymes, either secreted by the animal or by microbes harbored in the animal's gut, in digestion of foodstuffs. For the most part, the major success in use of dietary supplementation of exogenous enzymes in monogastric species has been achieved in the area of overcoming negative effects of antinutritional factors. In animals whose diet comprises primarily forages and other plant materials, the use of exogenous enzymes has focused on improvements in fiber digestion.

Plant materials contain significant proportions of insoluble, structural polysaccharides. Even such as ruminants and equine species adapted to subsist on a diet of plant materials, digestion of forages is often not complete. Overall feed digestibility and nutrient availability to the animal is not maximal, and the full benefit of consumption of forage is not realized, as reflected in animal performance. Accordingly, attempts at supplementation of animals with exogenous enzymes have been made. For example, U.S. Pat. No. 5,720,971 to Beauchemin et al. discloses a fibrolytic enzyme supplement, primarily containing cellulase and xylanase, which is sprayed on forages and allowed to incubate for a period of hours prior to ingestion. The result is a feed composition consisting of forages with improved digestibility for ruminant species. U.S. Pat. No. 5,948,454 to Virkki et al. teaches a modified cellulase-containing composition suitable for treating crops to improve storage characteristics and feed values.

The enzyme supplements cited above are generally effective for their intended purposes. However, further improvements are possible. For example, each of the enzyme supplements cited above are used as pretreatments of forages prior to feeding those forages to animals. This adds an additional step to the process, and may result in a feed which, though more digestible, has a limited shelf life and may require specialized storage conditions related to temperature or moisture sensitivity. Additionally, the potential for use of alternative enzymes for improvements in fiber digestibility, particularly in species whose diet comprises primarily forages or other fibrous feeds, has to date received limited study.

Esterases produced by various anaerobic bacteria and fungi are responsible for removing side groups normally present in plant cell wall polysaccharides. Other esterases such as feruloyl and coumaroyl esterases also break down chemical bonds central to hemicellulose-lignin associations. While not wishing to be bound to any particular theory, it is believed that the actions of esterases increase enzyme accessibility to the backbones of plant cell wall polysaccharides and influence overall plant cell wall structure, thereby improving digestibility. There remains a need in the art for improvements in the economics of agriculture, especially as related to animal feeds. This can be accomplished, at least in part, using alternative enzyme supplements for enhancing fiber digestibility in, e.g., ruminant, equine, porcine, and avian species. There is further a need in the art for alternative enzyme supplements capable of enhancing the efficacy of prior art enzyme supplements for enhancing fiber digestibility in, e.g. ruminant, equine, porcine, and avian species. Ruminant animals of particular economic importance include cattle, sheep, buffaloes and goats. Others include camels, guanaco, llamas, wapiti, antelope, musk oxen, giraffes and others. Improving the efficiency of feed utilization improves the economics of agriculture, thus providing a benefit to the agricultural industry and to society. In addition, captive wild ruminants and other fiber-eating animals can benefit from the present invention.

SUMMARY OF THE INVENTION

The present invention provides compositions comprising acetyl esterase; these compositions are useful for enhancing fiber digestion. The compositions can be used as dietary supplements for animals, especially for those animals with a fiber-rich diet. The animals which benefit from such supplements include, without limitation, ruminant, equine, porcine, caprine, ovine, and avian species, e.g., poultry. The acetyl esterase containing compositions can be dry formulations or wet formulations with crude fermentation materials or purified enzyme. In a specifically exemplified embodiment, the enzyme composition desirably is administered in an amount sufficient to provide from about 1 to about 10 U/kg of digesta in the rumen. The composition can be mixed with feed, silage, hay or grain, or it can be incorporated into mineral supplements to be fed to the animals or into a concentrated feed component for ease of mixing into the bulk feed preparation.

The acetyl esterase of the present invention may be isolated from an anaerobic microorganism, such a ruminal fungus or a ruminal bacterium. In a preferred embodiment, the acetyl esterase of the present invention may be isolated from or produced in cultures of anaerobic fungi including, but not limited to, Piromyces, Neocallimastix, Caecomyces, Anaeromyces and Orpinomyces, or combinations thereof. Alternatively, the acetyl esterase for use in the present invention may be isolated from cultures of or produced in anaerobic bacteria such as Butyrivibrio, Clostridium, Fibrobacter, Prevotella, Ruminobacter, Ruminococcus, Selenomonas or Streptococcus. Other potential bacterial sources of acetyl esterase include, but are not limited to, Bacillus, Pseudomonas, Streptomyces, Thermonospora, Caldocellum, Thermoanaerobacter, or combinations thereof. As specifically exemplified, the acetyl esterase is produced by a ruminal isolate of Orpinomyces, strain KY. The strain described herein does not produce detectable cellulase or xylanase activity in the extracellular milieu, although the majority of the acetyl esterase activity is extracellular.

Another aspect of the invention is a method for enhancing fiber digestion in an animal, mammalian or avian, by feeding an effective amount of an acetyl esterase-containing composition to said mammalian or avian species. The acetyl esterase containing composition of the present invention may be fed to any animal for which forages or fibrous foods comprise a significant percentage of the diet, with the proviso that there is sufficient acetyl esterase to improve the digestion of the plant fiber material in the diet of the animal. It is envisioned that for a ruminant, for example, a dairy cow, the acetyl esterase is fed in an amount sufficient to result in a specific activity in the rumen of about 1 to about 10 U/kg of digesta (rumen contents). Desirably, a mature bovine is fed from about 50 to about 5000 units of acetyl esterase per day, depending for example on diet and on whether a female bovine is lactating or not. The amount of enzyme activity to be consumed by the animal is determined by rumen (or other relevant digestive organ) capacity.

In yet another embodiment of the present invention, a method for enhancing fiber digestion in a mammal is provided comprising feeding an effective amount of an acetyl esterase-containing composition in conjunction with known, prior art enzyme supplements to said mammal to enhance fiber digestibility. The acetyl esterase-containing compositions of the present invention are especially useful in supplements to the diets of animals including, but not limited to, cattle, horses, sheep, goats, swine and poultry.

Also embodied within the present invention is the anaerobic fungus isolated from the rumen, which fungus is the specifically exemplified source of acetyl esterase. This fungus is a polycentric fungus, and without wishing to be bound by theory, it is believed to be a member of the genus Orpinomyces.

DETAILED DESCRIPTION OF THE INVENTION

Figure 1:
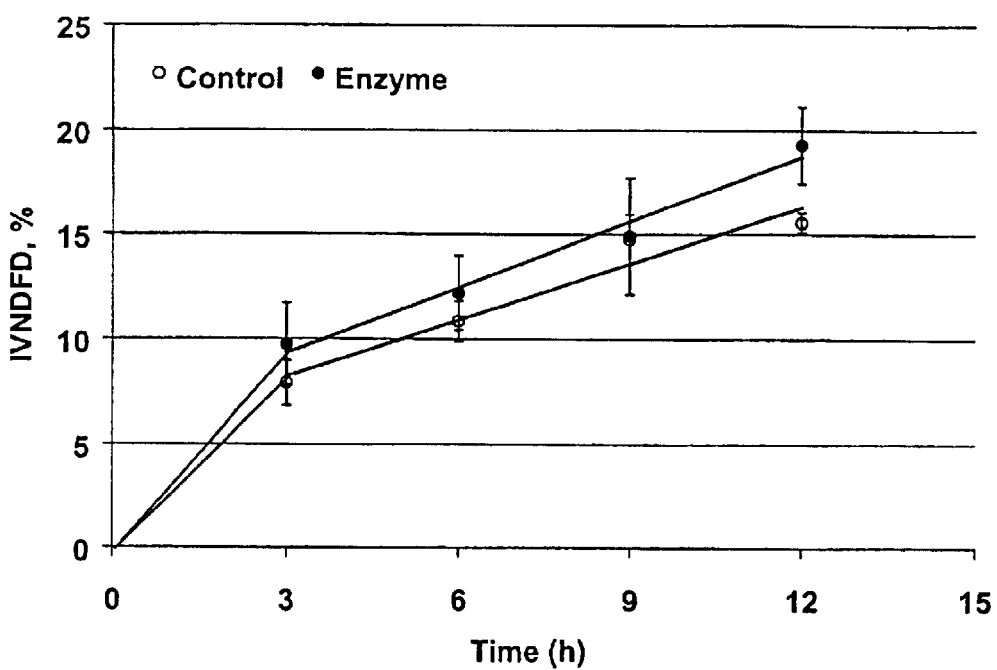
FIG. 1 shows effects of a freeze-dried fungal culture preparation on in vitro degradation of the neutral detergent fiber (NDF) fraction from a fescue hay-based diet by batch cultures of ruminal microorganisms.

As used in the present context, acetyl esterase includes one or more enzymes that hydrolyze p-nitrophenyl acetate to form p-nitrophenol and acetic acid. Thus, the present invention contemplates the use of one or more esterases with activity for p-nitrophenyl acetate as animal feed supplements to improve the digestion of a high fiber diet. Enzymes classified as acetyl esterases include, without limitation, xylan acetyl esterases, mannan acetyl esterases and rhamnogalacturonan acetyl esterases. Organisms other than Orpinomyces sp. strain KY that produce acetyl esterase(s) include, but are not limited to, other Orpinomyces isolates, *Neocallimastix patriciarum, Fibrobacter succinogenes, Streptomyces thermoviolaceus*, Streptomyces, Caldocellum, Butyrivibrio, Ruminobacter, Prevotella, Ruminococcus, Selenomonas and Streptococcus. Other bacterial sources of acetyl xylanase can include, without limitation, Bacillus, Pseudomonas, Streptomyces, Thermonospora, Thermoanaerobacterium and combinations thereof, and others. See, e.g., Christov, L. P. and Prior, B. A. 1993. *Enzyme Microb. Technol.* 15, 460-475 and references cited therein; Dalrymple, B. P. et al. 1997. *Microbiology* 143,2605-2614; and Blum, D. et al. 1999. *Appl. Environ. Microbiol.* 65, 3990-3995.

Exogenous supplementation of compositions containing acetyl esterases surprisingly improves fiber digestion by rumen microorganisms. Such supplementation similarly improves fiber digestion in animals consuming it. In particular, the compositions of the present invention improve neutral detergent fiber (NDF) digestion, production of volatile fatty acids (VFA), and kinetics of digestion. Animals whose diets comprise a substantial percentage of forages are particularly benefitted by the compositions of the present invention.

Accordingly, the invention provides compositions and methods for improving fiber digestion in animals utilizing an acetyl esterase enzyme-containing composition formulated for feeding to forage-consuming animals including, but not limited to, ruminant, equine, porcine, and avian species. The compositions and methods of the present invention may be accomplished by various means which are illustrated herein. These examples are intended to be illustrative only, as numerous modifications and variations will be apparent to those skilled in the art.

In a preferred embodiment, the compositions of the present invention comprise an acetyl esterase, wherein the amount of acetyl esterase in the composition is sufficient to produce an activity of from about 1 to about 10 U acetyl esterase/kg of digesta. The compositions of the present invention may be fed to any animal whose diet comprises a substantial percentage of forage or fibrous foods. Advantageously, the compositions of the present invention are fed to forage-consuming animals such as ruminant, equine, porcine, and avian species.

The acetyl esterase of the present invention is isolated from a ruminal microorganism, said microorganism having as its source a ruminant animal which has consumed a primarily forage-based diet. Ruminants from which the microorganism can be isolated include, but are not limited to, cattle, sheep, goats, and any other animal whose primary means of digesting fiber comprises the rumen and microorganisms contained therein. In one embodiment, the acetyl esterase of the invention is isolated from an anaerobic fungus of ruminal origin, Orpinomyces sp. strain "KY" herein. The anaerobic fungus may be selected from any of a number of fungi native to the rumen, including, but not limited to, Piromyces, Neocallimastix, Caecomyces, Anaeromyces and Orpinomyces. Other fungal sources of acetyl xylanase can include, without limitation, Aspergillus, Fusarium, Penicillium, Schizophyllum, Trichoderma, Rhodotorula and combinations thereof. In yet another embodiment, the acetyl esterase of the invention may be isolated from any of a number of bacteria native to the rumen, including, but not limited to, Butyrivibrio, Clostridium, Fibrobacter, Prevotella, Ruminobacter, Ruminococcus, Selenomonas and Streptococcus. Other bacterial sources of acetyl xylanase can include, without limitation, Bacillus, Pseudomonas, Streptomyces, Thermonospora, Caldocellum, Thermoanaerobacter and combinations thereof. The specifically exemplified isolate "KY" has been identified as a species of Orpinomyces.

Orpinomyces spp. KY has been deposited by Applicants with the American Type Culture Collection, 10801 University Avenue, Manassas, Va. 20110. The sample deposited with the ATCC is propagated from the same specimen maintained since prior to the filing date of this application.

The deposits will be maintained without restriction in the ATCC depository for a period of 30 years or 5 years after the most recent request, or for the effective life of the patent, whichever is longer, and will be replaced if the deposit becomes non-viable during that period. This strain was assigned Accession No. PTA-4235.

Concentrated wet and dry preparations derived from fermentation of the "KY" isolate are described hereinbelow. Desirably, the acetyl esterase containing preparation is a dry preparation. The dry preparation can be formulated with mineral supplements formulated for improving animal nutrition such that an appropriate amount of minerals and the "KY" preparation are ingested each day by the animal in which fiber digestion is being improved. Where pelleted feed is used, one of ordinary skill in the art can coat clay particles with milled dry fermentation material containing acetyl esterase(s), and then mix the coated clay particles with the pelleted feed. The procedures followed in U.S. Provisional Application 60/346,127 (filed Jan. 4, 2002), which is incorporated by reference herein, can be followed for the present dried preparations containing acetyl esterase with adjustments for the relative amount of said preparations and the animal to be fed.

Alternatively, the dry "KY" preparation can be mixed with a concentrated feed component, and then that combination can be mixed with a total mixed ration or other feed. It is easier to obtain thorough mixing when a relatively small amount of enzyme containing preparation is pre-mixed in some feed component, carrier or dietary supplement such as a mineral supplement. In another situation, the acetyl esterase supplemented feed concentrate, for example, a grain, can be fed directly to the animal.

For mature cattle, each should consume about 50 to about 5000 units of acetyl esterase per day to obtain the beneficial effect of the esterase of the present invention on fiber digestion. Where liquid formulations are utilized, similar administration rates are contemplated, with adjustments made for the concentration of active enzyme in the formulation. For other animals, the units consumed is adjusted to the volume of the organ of digestion. For ruminants, it is appropriate to feed a sufficient quantity of enzyme supplement to provide from about 1 to about 10 units of enzyme per kg of digesta.

All references cited in the present application are incorporated by reference in their entireties to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Ruminal digesta was obtained from a ruminally fistulated cow which had been fed a forage-based diet as shown in Table 1.

TABLE 1

Composition of diets fed to the rumen-fistulated animals

| Components | Composition % (DM basis) | |
|---|---|---|
|  | Forage-based diet | Concentrate-based diet |
| Fescue hay | 77.86 | 37.23 |
| Dry rolled corn | 11.72 | 49.64 |
| Soybean meal | 8.08 | 7.54 |
| Limestone | 0.54 | 0.63 |
| Trace mineral premix | 0.44 | 0.44 |
| Vitamin premix | 0.05 | 0.04 |
| Molasses | 1.30 | 4.48 |

An anaerobic fungus ("KY") was isolated from the ruminal digesta using the Hungate roll tube technique [Joblin, K. N. 1981. Isolation, enumeration, and maintenance of rumen anaerobic fungi in roll tubes. *Appl. Environ. Microbiol.* 42,6:111–1122]. Serial dilutions of fresh rumen fluid were prepared inside an anaerobic chamber. Rumen fluid dilutions were used to inoculate roll tubes in triplicate. The media used was modified rumen fluid-based medium [Obispo, N. E. and Dehority, B. A. 1992. A most probable number method for enumeration of rumen fungi with studies on factors affecting their concentration in the rumen. *J. Microbiol. Methods* 16, 259-270].

Roll tubes were incubated at 39° C. until fungal colonies developed. Individual colonies were transferred to tubes containing liquid rumen fluid-based media with antibiotics. Once a pure culture was established, the fungus was transferred to modified medium 10 liquid broth without antibiotics and with glucose as the sole carbohydrate. Modified medium 10 contains (per liter) 2.0 g Trypticase (Becton Dickinson, Cockeysville, Md.), 0.5 g yeast extract (Difco, Detroit, Mich.), 225 mg $K_2HPO_4$, 225 mg $KH_2PO_4$, 450 mg $(NH_4)_2SO_4$, 450 mg NaCl, 45 Mg $MgSO_4*H2O$, 45 mg $CaCl_2*H_2O$, 1.0 mg hemin, 1.7 ml acetic acid, 0.6 ml propionic acid, 0.4 ml butyric acid, 0.1 ml isobutyric acid, 0.1 ml n-valeric acid, 0.1 ml iso-valeric acid, 0.1 ml 2-methylbutyric acid, 1.0 mg resazurin, 0.5 g L-cysteine HCl, 4.0 g $Na_2CO_3$ and 0.5 g agar (Bacto-agar, Difco). This medium contains agar to prevent aggregation and compact fungal growth that interferes with transfer by injection.

The Orpinomyces isolate "KY" was maintained at 39° C. in modified medium 10 liquid broth containing glucose or cellobiose by subculturing every 4 to 5 days. Modified medium 10 containing glucose, cellobiose or filter paper was used for growth of the fungus and production of fungal-derived enzyme preparations as described infra. Soluble carbohydrates (glucose or cellobiose) were added directly during media preparation, or sterile concentrated carbohydrate solutions were injected into culture tubes before fungal inoculation. Filter paper was weighed directly into Hungate tubes or serum bottles prior to the addition of media. Growth of the fungal isolate in Hungate roll tubes was monitored microscopically.

Upon microscopic observation, the "KY" fungal isolate exhibited a polycentric form of thallus development. Further examination revealed a highly branched filamentous rhizoid growth habit, and the thicker hyphae sometimes contained septa. The liberation of zoospores was not required for growth and maintenance of the fungal isolate. Young sporangia initially appeared translucent and were round or elliptical in shape. The appearance of the sporangia became refractive as they developed. Mature sporangia were generally spherical and contained numerous zoospores. Numerous zoosporangia developed per thallus; however, release of zoospores was not observed during culture in the laboratory. Large spherical colonies were often seen in liquid culture. Metabolically active colonies were bright white and generally floated to the surface of the culture medium, but darkened and sank to the bottom of the cultures as they aged. Growth in liquid culture was supported by glucose, cellobiose, birchwood xylan, Whatman no. 1 filter paper or wheat bran as a source of carbon and energy. Based on these morphological characteristics, this particular isolate is assigned to the Orpinomyces genus [Barr, D. J. S. 1988. How modem systematics relates to the rumen fungi. Biosystems 21:351-356]. Somewhat surprisingly, there was no measurable cellulase or xylanase in the extracellular environment of cultures or in the mycelial material. The acetyl esterase produced by the present isolate is distributed between the extracellular environment (75%) and mycelial material (25%).

Acetyl esterase preparations useful in the compositions and methods of the present invention may be prepared and stored by any of a number of means known in the art, including lyophilization of entire fungal cultures, lyophilization of supernatants derived from said fungal cultures, and preparation of a liquid enzyme fraction from culture material. Koji fermentations, as well known to the art, can also be used to produce the acetyl esterase of the present invention, especially if carried out under anaerobic conditions. For supplementation of animal feeds, the dried acetyl esterase containing preparations can be incorporated with mineral supplements, feed, feed concentrates, such that the amount of enzyme consumed results in from about 1 to about 10 units per kg digesta, especially in the rumen. The activity of acetyl esterase in a dried preparation is often about 0.5 to about 5 units/gram of dried material.

Example 2

The acetyl esterase preparations of the present invention are produced by freeze-drying a fungal culture. The anaerobic fungal isolate, prepared as described in Example 1, was grown for 6 d in modified medium 10 containing glucose. The entire culture was poured into aluminum pans and frozen at −80° C. The frozen culture was lyophilized. Total protein and acetyl esterase activities of the fungal lyophilate were determined after reconstitution. Total protein was determined by the method of Bradford, [Bradford, M. 1976. Anal. Biochem. 72, 248-254] and acetyl esterase activity was determined by measuring the amount of p-nitrophenol released from p-nitrophenyl acetate by following $A_{405}$ over time. Acetyl esterase activity in fungal lyophilate=1.27 U/g.

Acetyl esterase was measured using an assay previously described [Huggins and Lapides. 1947. Acyl esters of p-nitrophenol as substrates for the colorimetric determination of esterase. J. Biol. Chem. 170, 467-482]. A fresh standard stock solution was prepared by dissolving 0.070 g p-nitrophenol (pNP) in 100 ml deionized disilled water. A standard curve was prepared under assay conditions by substituting standard dilutions for enzyme and 10% ethanol for substrate working solutions. The final concentration of pNP in the standard curve ranged from 50-300 $\mu$M. A 50 mM stock solution of p-nitrophenyl acetate (pNA) was prepared by dissolving 0.045 g pNA in 5 ml ethanol. The pNA stock colution was kept at 4° C. for up to 5 days. The pNA substrate working solution (5 mM pNA in 10% ethanol) was prepared by diluting 1 ml of stock solution to 10 ml with water. Reactions were performed in 1.5 ml polystyrene semi-micro cuvettes (Fisher Scientific, Pittsburgh, Pa.) by adding 0.8 ml reaction buffer (100 mM potassium phosphate pH 6.5) and 0.1 ml of an appropriate enzyme dilution. Substrate working solution (0.1 ml) was added at precise time intervals to start the reactions. Reaction volume was 1.0 ml, and the buffer and substrate concentrations were 80 mM and 0.5 mM, respectively. Absorbance at 405 nm was recorded at 5 min intervals for 20 min. Substrate blanks were included by substituting water in place of enzyme solution. Because enzymatic activity is estimated from the rate of absorbance increase over time, enzyme blanks for each enzyme dilution and time zero absorbance were not required.

For routine determination of acetyl esterase activity in large numbers of samples, the procedure described was adapted for use with 96 well microtiter plates (Nalge Nunc International, Rochester, N.Y.). Serial dilutions of each sample (100 $\mu$l) were prepared in triplicate in microtiter plates. Buffer (80 $\mu$l, 200 mM potassium phosphate, pH 6.5) and substrate working solution (20 $\mu$l) were added to start the reactions. The final reaction volume was 200 $\mu$l. The microtiter plates were placed in a Perkin Elmer HTS7000 Bio Assay Reader (Perkin Elmer Corporation, Norwalk, Conn.), and absorbance at 405 nm was measured every 5 min over a 20 min incubation period. Rates for all reactions and substrate blanks were expressed as $\Delta A_{405}$ per hour. Corrected rates were obtained by subtracting the average substrate blank rate from all enzyme reaction rates. The rate of pNP release in each reaction was estimated from the pNP standard curve using corrected reaction rates. Acetyl esterase activity was expressed as units per ml or per gram of enzyme preparation. One unit of acetyl esterase releases 1 $\mu$mol of pNP per min.

Example 3

The acetyl esterase enzyme can be produced by freeze-drying fungal culture supernatant. A fungal culture prepared as described in Example 1 was harvested after growth for 5 d in modified medium 10 containing glucose. Fungal biomass was separated from the culture supernatant by centrifugation. The supernatant was collected into aluminum pans, lyophilized, and stored at −20° C. Total protein and acetyl esterase activities of the fungal supernatant were determined as described in Example 2. There was some loss of acetyl esterase activity in the lyophilized material. Acetyl esterase specific activity in fungal supernatant=0.41 U/g protein.

Example 4

A liquid enzyme preparation can be utilized. The liquid acetyl esterase preparation produced by growing the fungal isolate, prepared as in Example 1, in 9.5 L flasks. Basal medium 10 was used throughout the scale-up process and during acetyl esterase production. Cellobiose was used as the growth substrate in the scale-up process. Filter paper was used as a substrate during enzyme production in the final large scale culture.

For production conditions, ruminal anaerobic fungi were grown in medium 10 containing filter paper as the sole carbon source for acetyl esterase production. The production culture was incubated at 39° C. under anaerobic conditions. After growth for 7 days, the culture was filtered. The filtrate was centrifuged to remove fungal mycelia and undigested filter paper residue, and the proteins (including the extracellular enzymes) in the supernatant were concentrated about 40-fold by ultrafiltration. Total protein and acetyl esterase activities of the liquid enzyme product were determined as described in Example 2. Acetyl esterase activity in the liquid enzyme product=0.57 U/ml of concentrate. It is noted that there was some loss of acetyl esterase activity in the concentrated material as compared to the starting material.

A composition comprising an acetyl esterase enzyme is used to improve fiber digestion in a mammal consuming it. In preferred embodiments of the invention, improvement in fiber digestion is determined by measuring increased VFA production and hexose utilization. Improvement in fiber digestion is also determined by measuring increased NDF digestion.

Example 5

The effects of exogenous enzyme preparations on in vitro fermentation and digestibility of feed were examined in batch cultures of mixed ruminal microorganisms using a modification of the procedure described by Tilley and Terry [Tilley, J. M. A. and R. A. Terry. 1963. A two stage technique for the in vitro digestion of forage crops. J. Br. Grassl. Soc. 18:104-109]. Cultures were established with rumen contents obtained from ruminally fistulated animals receiving forage-based diets (Table 1).

Fresh rumen fluid obtained from a ruminally-fistulated animal was strained through cheesecloth and placed inside an anaerobic glove box containing an atmosphere of 10% $H_2$, 20% $CO_2$ and 70% $N_2$. Inocula were prepared inside this anaerobic chamber using equal volumes of strained rumen fluid and McDougall's artificial saliva solution. The mixture was blended, placed in a sealed flask, removed from the anaerobic chamber and used to inoculate culture media.

Batch cultures were established in 100-mL serum bottles containing 0.5 g of a forage-based diet (Table 1. Anaerobic conditions were maintained in the inoculum. Cultures were incubated in a water bath at 39° C. with continuous agitation. Exogenous enzyme preparations were added to treated cultures as aqueous solutions immediately prior to inoculation. Control cultures received deionized, distilled water.

Volatile fatty acid production was used to examine the effects of a freeze-dried fungal culture on digestion of a fescue hay-based diet. Serum bottle cultures prepared as described supra were supplemented with increasing concentrations of the fungal preparation to include acetyl esterase activities ranging from 0 to 2.54 units/L. Samples were collected after incubation at 39° C. for 12 h for determination of VFA concentrations. Total VFA production, individual VFA proportions and hexose utilization were determined by gas chromatography as is known in the art. Volatile fatty acids produced by each culture were determined by subtracting the average VFA concentrations at 0 h from the VFA concentrations after in vitro incubation. Hexose utilization was estimated stoichiometrically from VFA production by calculating the theoretical fermentation balance [Wolin, J. 1960. A theoretical rumen fermentation balance. J. Dairy Sci. 43:1452-1459].

The addition of a freeze-dried fungal preparation to ruminal in vitro cultures at concentrations between 0.127 and 2.54 units acetyl esterase/L increased (P<0.05) h total VFA production and hexose utilization rates measured 12 hours after inoculation from a fescue hay-based diet (Table 2). The production of acetate, propionate and butyrate increased with acetyl esterase supplementation at 0.127 and 2.54 units/L. However, the addition of lyophilized fungal preparation at the concentration representing 2.54 units acetyl esterase/L also reduced (P<0.05) the A:P ratio.

TABLE 2

Effects of a freeze-dried fungal culture containing acetyl esterase activity on 12 h in vitro VFA production and hexose utilization from a fescue hay-based diet by batch cultures of ruminal microorganisms

| | Acetyl esterase activity (units/L) | | | | | | | |
|---|---|---|---|---|---|---|---|---|
| Item | 0 | 0.127 | 0.254 | 0.635 | 1.27 | 1.91 | 2.54 | SEM |
| VFA production (mmoles/L) | | | | | | | | |
| Total VFA | 36.4 | 39.8[a] | 35.7 | 36.6 | 36.1 | 2937.7 | 40.9[a] | 0.77 |
| Acetate | 23.6 | 25.5[a] | 22.5 | 22.3 | 22.3 | 23.2 | 25.2[a] | 0.53 |
| Propionate | 7.7 | 8.3[a] | 7.4 | 7.4 | 7.6 | 7.9 | 8.5[a] | 0.17 |
| Butyrate | 3.6 | 3.9[a] | 3.5 | 3.5 | 3.6 | 3.8 | 4.1[a] | 0.15 |
| A:P ratio | 3.1 | 3.1 | 3.0 | 3.0 | 2.9 | 2.9 | 2.9* | 0.04 |
| Hexose utilization rate(mmoles $*L^{-1} *h^{-1}$) | 1.72 | 1.85[a] | 1.64 | 1.64 | 1.65 | 1.73 | 1.88[a] | 0.04 |

[a]Means (n = 3) in the same row with a superscript are different from unsupplemented culture means (P < 0.05).

Example 6

Effects of a fungal lyophilate prepared as described in Example 2 on NDF digestion were determined. The Daisy$^{II}$ in vitro incubation system (Ankom Technology Corp., Fairport, N.Y.), an automated in vitro fermentation system used for sequential NDF and ADF analysis, was used to examine the effects of the fungal lyophilate on NDF digestion. Substrate (fescue hay-based diet) was placed in individual filter bags. The bags were then heat-sealed and incubated in 2-L jars containing rumen fluid and buffer inside a fermentation chamber with agitation and temperature controls (39° C.). Exogenous enzyme preparations were added directly to digestion jars as a powder or an aqueous solution. Jars not receiving an enzyme supplement served as controls. Rumen fluid inoculum was added to each equilibrated jar to start the digestion. The fungal lyophilate was added to treated cultures at a rate of 0.51 units acetyl esterase/L. Rates of NDF digestion were estimated by measuring NDF disappearance in samples incubated with agitation for 3, 6, 9, and 12 hours.

Greater NDF digestion was observed after 12 h incubation in cultures supplemented with the freeze-dried fungal preparation than in unsupplemented cultures (FIG. 1). However, the rates of NDF digestion ex vivo calculated for the 3 to 12 h incubation period did not differ between supplemented and unsupplemented cultures.

Calculation of approximate rates of NDF digestion for the initial 3 h period of incubation (from NDF disappearances at 3 h) revealed that acetyl esterase supplementation increased the initial rate of NDF digestion (9.75 vs. 7.89% for enzyme-supplemented and unsupplemented cultures, respectively; FIG. 1). These findings indicate that the statistically significant effects of acetyl esterase supplementation on in vitro NDF digestion occur during the initial stages of fermentation.

Example 7

The effects of fungal culture supernatant on in vitro digestion of a fescue hay-based diet were examined. The freeze-dried fungal culture supernatant was added to serum bottle cultures at concentrations of from 0 to 2.05 units acetyl esterase/L. Total VFA production, hexose utilization, and acetate to propionate (A:P) ratio were determined as discussed in Example 5 after a 12 hour incubation period. Total VFA production was greater in cultures supplemented with freeze-dried culture supernatant at concentrations greater than 1.23 units acetyl esterase/L than in unsupplemented cultures (Table 3). The addition of fungal culture supernatant also enhanced hexose utilization rates when present at 1.64 and 2.05 units acetyl esterase/L. No effects were observed on the A:P ratio due to the addition of lyophilized fungal culture supernatant. The addition of the fungal-derived preparation at a concentration of 1.23 units acetyl esterase/L increased acetate and propionate production. Supplementation at 1.64 and 2.05 units acetyl esterase/L also enhanced the production of butyrate.

TABLE 3

Effects of lyophilized fungal culture supernatant containing acetyl esterase (AE) activity on 12 h in vitro VFA production and hexose utilization rate from a fescue hay-based diet by batch cultures of ruminal microorganisms

| Enzyme (AE units/L) | VFA production (mmoles/L) | | | | A:P ratio | Hexose utilization rate (mmoles/L*h) |
|---|---|---|---|---|---|---|
| | Total | Acetate | Propionate | Butyrate | | |
| 0 | 52.9$^a$ | 34.2$^a$ | 9.5$^a$ | 5.9$^a$ | 3.61 | 2.42$^a$ |
| 0.082 | 49.6$^a$ | 32.5$^a$ | 8.8$^a$ | 5.4$^a$ | 3.70 | 2.27$^a$ |
| 0.164 | 52.6$^a$ | 34.2$^a$ | 9.4$^a$ | 5.7$^a$ | 3.63 | 2.40$^a$ |
| 0.205 | 49.0$^a$ | 32.9$^a$ | 9.0$^a$ | 5.0$^b$ | 3.66 | 2.28$^a$ |
| 0.410 | 49.0$^a$ | 32.7$^a$ | 8.9$^a$ | 5.0$^b$ | 3.67 | 2.26$^a$ |
| 0.615 | 51.8$^a$ | 34.1$^a$ | 9.5$^a$ | 5.5$^a$ | 3.60 | 2.38$^a$ |
| 0.820 | 56.4$^a$ | 36.4$^a$ | 10.2$^a$ | 6.0$^a$ | 3.57 | 2.56$^a$ |
| 1.230 | 59.2$^b$ | 38.0$^b$ | 10.7$^b$ | 6.2$^a$ | 3.55 | 2.68$^a$ |
| 1.640 | 63.4$^c$ | 40.4$^c$ | 11.4$^c$ | 6.8$^c$ | 3.54 | 2.85$^b$ |
| 2.050 | 65.7$^c$ | 42.0$^c$ | 11.7$^c$ | 6.8$^c$ | 3.61 | 2.94$^b$ |
| SEM | 1.22 | 0.72 | 0.20 | 0.21 | 0.03 | 0.05 |

$^{a,b,c}$ Means within the same column lacking a common letter differ (P < 0.01).

Example 8

The kinetics of VFA production from acetyl esterase supplemented and unsupplemented cultures were examined using serum bottle cultures. Fescue hay-based diet (0.5 g) in filtered rumen fluid and artificial saliva as described above was used as the substrate. Liquid fungal preparation prepared as in Example 4 was added to enzyme supplemented cultures at concentrations up to 11.4 units acetyl esterase/L. All cultures were incubated in a shaking water bath at 39° C. Samples were taken from each culture after incubation at intervals up to 12.0 h. Total VFA production and hexose utilization rates were determined as described.

Total VFA production and hexose utilization rates were greater in cultures supplemented with liquid fungal preparation than in unsupplemented control cultures (Table 4). Enzyme effects on total VFA production observed after acetyl esterase supplementation were mainly due to enhanced acetate production without a significant change in propionate and butyrate production. These changes in the relative proportions of VFA produced are reflected in greater A:P ratios in cultures supplemented with liquid fungal preparation at acetyl esterase concentrations greater than 0.57 units/L. Production of propionate and butyrate only increased in cultures receiving of 11.4 units acetyl esterase/L. In addition, the proportions of isoacids were greater in cultures supplemented with more than 0.057 units acetyl esterase/L than in unsupplemented cultures.

The effects of acetyl esterase-containing preparations were reflected in greater production of acetate, propionate and butyrate. In general, acetyl esterase activities did not seem to change the relative proportions of VFA produced except at a high concentration of the enzyme-containing supplement. Isoacids or branched-chain volatile fatty acids are most likely produced by certain proteolytic ruminal bacteria from degradation of the branched-chain amino acids valine, leucine and isoleucine [Allison, M. J. 1978. Production of branched-chain fatty acids by certain anaerobic bacteria. *Appl. Environ. Microbiol.* 35:872-877]. In addition, isoacids are absorbed and used by cellulolytic ruminal bacteria for de novo synthesis of branched-chain amino acids [Allison, M. J. 1969. Biosynthesis of amino acids by ruminal microorganisms. *J. Animal Sci.* 29:797-807; Robinson I. M. and Allison M. J., 1969. Isoleucine biosynthesis from 2-methylbutyric acid by anaerobic bacteria from the rumen. *J. Bacteriol.* 97:1220-1226].

Consequently, the concentrations of isoacids reflect the rates of protein degradation and isoacid absorption by ruminal microorganisms. Since hexose utilization rate was greater in enzyme-supplemented cultures, the changes observed in the proportions of isoacids are certainly indicative of enhanced protein digestion in these cultures. However, beneficial effects on fermentation were generally observed with acetyl esterase concentrations as low as 1 or 2 units/L.

Example 9

Figure 3:
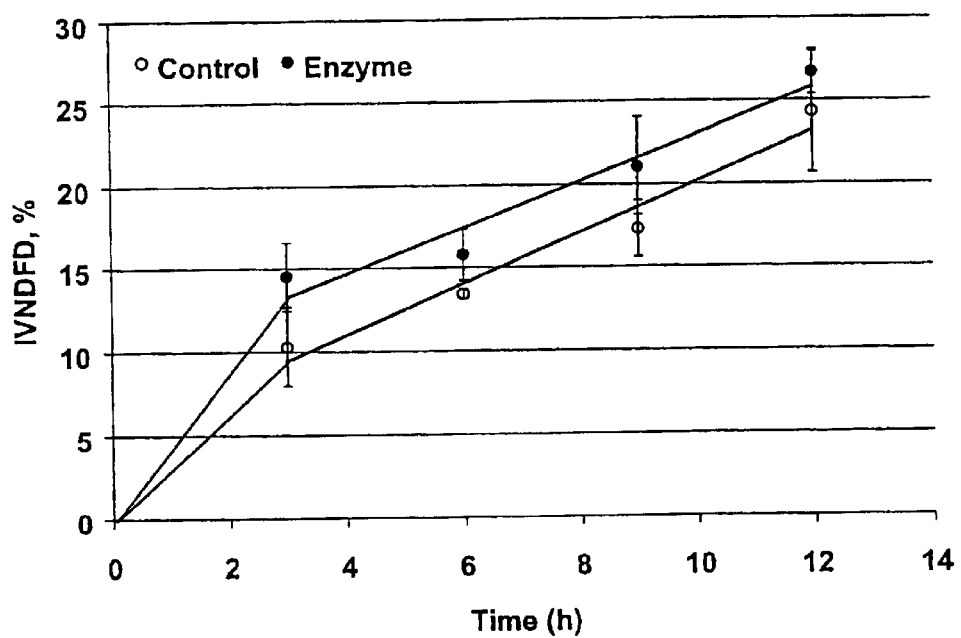
FIG. 3 shows effects of a liquid enzyme preparation containing acetyl esterase activity on in vitro digestion of the NDF fraction from a fescue hay-based diet in batch cultures of ruminal microorganisms.

The Daisy$^{II}$ incubation system was used to examine the effects of the liquid fungal-derived preparation (prepared as in Example 4) containing acetyl esterase on in vitro digestion of the NDF fraction of a fescue hay-based diet as described in Example 6. Enzyme treated cultures in the Daisy$^{II}$ incubation system received 1.14 units acetyl esterase/L. NDF digestibility tended to be greater in cultures supplemented with the acetyl esterase-containing preparation after in vitro incubation for 3, 6, 9 and 12 h than in unsupplemented cultures (FIG. 3). The rates of NDF digestion calculated for the 3 to 12 h incubation period did not differ between control and enzyme-treated cultures (Table 5).

TABLE 4

Effects of a liquid acetyl esterase (AE) enzyme preparation on 12 h in vitro VFA production and hexose utilization from a fescue hay-based diet by batch cultures of ruminal microorganisms.

| Enzyme (AE units/L) | VFA production (mmoles/L) | | | | A:P ratio | Isoacids proportion (mol/mol) | Hexose utilization rate (mmoles*L$^{-1}$*h$^{-1}$) |
|---|---|---|---|---|---|---|---|
| | Total | Acetate | Propionate | Butyrate | | | |
| 0 | 41.3 | 25.2 | 8.0 | 5.9 | 3.16 | 0.054 | 1.93 |
| 0.029 | 41.7 | 25.2 | 8.1 | 5.9 | 3.10 | 0.059 | 1.94 |
| 0.057 | 39.4 | 23.4 | 7.6 | 5.3 | 3.09 | 0.077$^b$ | 1.80 |
| 0.086 | 37.6$^a$ | 22.8$^a$ | 7.0$^b$ | 4.8$^b$ | 3.26 | 0.077$^b$ | 1.71$^b$ |
| 0.114 | 33.9$^c$ | 20.4$^c$ | 6.4$^c$ | 4.1$^c$ | 3.18 | 0.088$^c$ | 1.53$^c$ |
| 0.285 | 35.2$^c$ | 21.5$^c$ | 6.6$^c$ | 4.3$^c$ | 3.28 | 0.079$^c$ | 1.59$^c$ |
| 0.570 | 38.7 | 23.5 | 6.9b$^b$ | 4.9$^b$ | 3.39$^b$ | 0.087$^c$ | 1.73$^c$ |
| 0.855 | 45.7$^a$ | 27.4$^a$ | 7.6 | 6.1 | 3.59$^c$ | 0.100$^c$ | 2.00$^a$ |
| 1.140 | 43.0 | 27.0 | 7.4 | 5.4 | 3.66$^c$ | 0.073$^c$ | 1.94 |
| 2.850 | 46.7$^b$ | 29.1$^c$ | 8.0 | 5.8 | 3.64$^c$ | 0.082$^c$ | 2.09$^a$ |
| 5.700 | 49.9$^c$ | 31.1$^c$ | 8.4 | 6.0 | 3.71$^c$ | 0.087$^c$ | 2.22$^c$ |
| 8.550 | 51.6$^c$ | 31.9$^c$ | 8.4 | 6.0 | 3.77$^c$ | 0.102$^c$ | 2.25$^c$ |
| 11.400 | 58.8$^c$ | 35.3$^c$ | 9.5$^c$ | 7.3$^c$ | 3.71$^c$ | 0.114$^c$ | 2.53$^c$ |
| SEM | 1.16 | 0.69 | 0.23 | 0.22 | 0.05 | 0.005 | 0.64 |

$^{a,b,c}$Superscripts within the same column indicate a difference between means (n = 3) from enzyme-supplemented and unsupplemented cultures ($^a$P < 0.05; $^b$P < 0.01; $^c$P < 0.001).

The addition of fungal-derived enzyme preparations containing acetyl esterase activity enhanced 12 h in vitro ruminal fermentation of a fescue hay-based diet as indicated by greater VFA production and hexose utilization rates. The effects of acetyl esterase-containing preparations were reflected in greater production of acetate, propionate and butyrate. In general, acetyl esterase activities did not seem to change the total VFA produced. The liquid acetyl esterase preparation did increase the acetate to propionate ratio by improving acetate production without affecting the production of propionate. The addition of liquid acetyl esterase preparation also increased the proportion of isoacids produced in vitro by batch cultures of ruminal microorganisms. Isoacids or branched-chain volatile fatty acids are most likely produced by certain proteolytic ruminal bacteria from degradation of the branched-chain amino acids valine, leucine and isoleucine (Allison, 1978, supra). In addition, isoacids are absorbed and used by cellulolytic ruminal bacteria for de novo synthesis of branched-chain amino acids (Allison, 1969; Robinson and Allison, 1969 supra).

TABLE 5

Effects of a liquid acetyl esterase-containing preparation on the rate of NDF digestion from a fescue hay-based diet during the initial 3 to 12 h of incubation.

| Treatment | NDF digestion rate (%/h) | Confidence intervals (%/h) | |
|---|---|---|---|
| | | Low 95% | Up 95% |
| Control | 1.54 | 0.78 | 2.30 |
| Enzyme | 1.40 | 0.69 | 2.10 |

Figure 2:
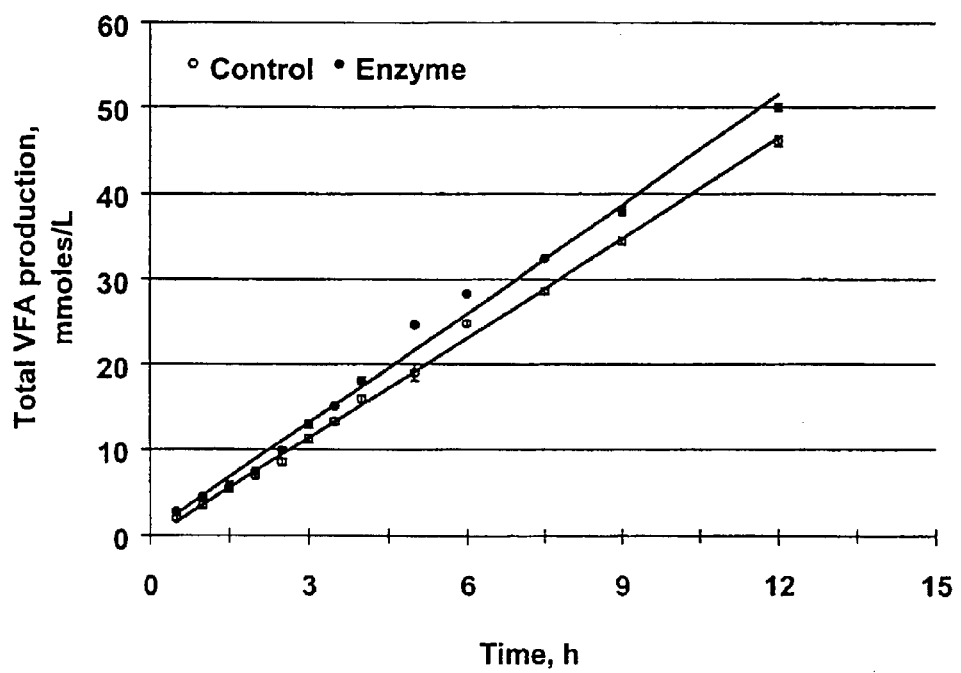
FIG. 2 shows effects of a liquid enzyme preparation containing acetyl esterase activity on in vitro volatile fatty acid (VFA) production from a fescue hay-based diet in batch cultures of ruminal microorganisms.

The effects of the liquid fungal-derived acetyl esterase preparation on the kinetics of total VFA production from a fescue hay-based diet during in vitro incubation for 12 h are shown graphically in FIG. 2. Total VFA production was greater in acetyl esterase-supplemented cultures than in unsupplemented cultures during 2.5 to 12 h incubation, but the rates of total VFA production were not statistically different between the two types of cultures.

Example 10

The following studies were designed to examine the effects of supplemental exogenous enzyme preparations on the initial rate and the kinetics of digestion of ruminant feed in batch cultures, and to test the usefulness of selected enzymatic preparations for modifying microbial digestion of feed in rumen-simulating continuous cultures.

The production of gas resulting from in vitro fermentation of feed by ruminal microbial cultures was used to examine digestion kinetics. Gas production was determined indirectly by measuring the increase in pressure over time in closed incubation bottles. An automated system was used in which individual pressure sensors (PRS2001-30A, Point Six Inc., Lexington, Ky.) remained attached to culture bottles throughout the entire incubation period.

A ruminally-fistulated steer fed an alfalfa hay based diet (Table 6) was used as the rumen fluid donor in all experiments. Rumen contents were collected 2 h after feeding and filtered through either four layers of cheesecloth. The inocula were prepared inside an anaerobic glove box by mixing strained rumen fluid and McDougall's artificial saliva solution. A fescue hay based diet (Table 1) was used as the substrate. Ruminal microbial cultures were established in serum bottles as in Example 5. The liquid acetyl esterase preparation prepared as in Example 4 was added to supplemented cultures immediately prior to rumen fluid inoculation. The cultures were then placed in a shaking water bath at 39° C. and pressure sensors were connected by inserting 20 gauge needles through the stoppers. The effects of supplemental acetyl esterase containing preparations on digestion kinetics of a fescue hay-based diet were examined in cultures of ruminal microorganisms during 12 h incubations.

TABLE 6

Composition of the diet fed to the fistulated steer used as the rumen fluid donor for gas production studies

| Component | Composition % (DM basis) |
| --- | --- |
| Alfalfa cubes | 80.00 |
| Dry rolled corn | 18.56 |
| Mineral premix | 0.40 |
| Vitamin premix | 0.04 |
| Molasses | 1.00 |

Pressure accumulation data were converted to gas volume (mL) produced by each culture using the Ideal Gas Law. Gas production rates were estimated for each treatment by fitting a linear regression using gas accumulation data from 0 to 3 h (3 h rate) or 0 to 12 h (12 h rate).

Figure 4:
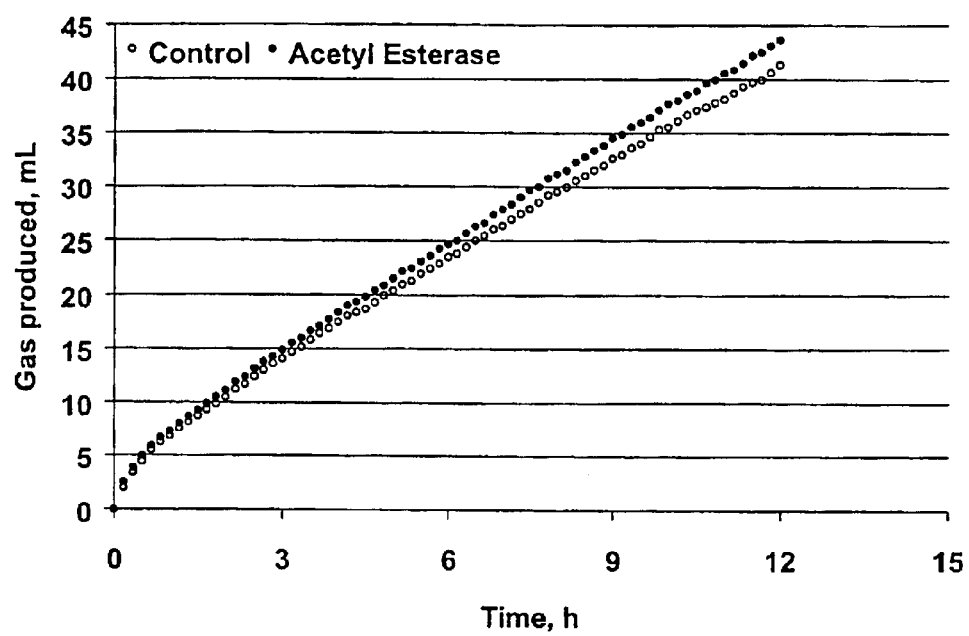
FIG. 4 shows cumulative gas production in cultures established with a fescue hay-based diet with or without supplementation of a liquid enzyme preparation containing acetyl esterase activity.

Gas production profiles of acetyl esterase supplemented and unsupplemented cultures are shown in FIG. 4. Gas production took place at a rapid rate during the initial period of fermentation and decreased as the incubations progressed. Rates of gas production remained constant after incubation for 3 h until fermentation was stopped at 12 h.

The addition of acetyl esterase to in vitro ruminal cultures enhanced the rates of gas production after incubation for 3 h (Table 7). In addition, the rates of gas production were 5.7% greater in acetyl esterase supplemented cultures than in unsupplemented cultures after incubation for 12 h (Table 8).

TABLE 7

Effects of exogenous enzyme preparations on the 3 h rate of gas production from a fescue hay-based diet by batch cultures of ruminal microorganisms

| Enzyme supplement[a] | Gas production rate (mL/h) | Confidence intervals (mL/h) | |
| --- | --- | --- | --- |
| | | Low 95% | Up 95% |
| Control | 4.18 | 4.04 | 4.33 |
| Acetyl esterase | 4.32 | 4.26 | 4.39 |

[a]Supplemental acetyl esterase was added at 0.7 units/L.

TABLE 8

Effects of exogenous enzyme preparations on the 12 h rate of gas production from a fescue hay-based diet by batch cultures of ruminal microorganisms

| Enzyme supplement[a] | Gas production rate (mL/h) | Confidence intervals (mL/h) | |
| --- | --- | --- | --- |
| | | Low 95% | Up 95% |
| Control | 3.16 | 3.15 | 3.18 |
| Acetyl esterase | 3.34 | 3.32 | 3.35 |

[a]Supplemental acetyl esterase was added at 0.7 units/L.

Our results suggest that supplementation of exogenous acetyl esterase has an important role during the initial period of fermentation by reducing the time required to make insoluble substrates available for microbial fermentation.

In a presently preferred embodiment of the present invention, the acetyl-esterase containing composition of the present invention may be utilized in conjunction with known prior art fibrolytic enzyme supplements. In a particularly preferred embodiment, the acetyl esterase-containing composition of the present invention may be combined with a cellulase/xylanase containing preparation, e.g. FIBROZYME™ (Alltech, Inc., Nicholasville, Ky.). Surprisingly, the acetyl esterase-containing composition of the present invention in combination with, e.g. FIBROZYME™, resulted in significant improvements in fibrolytic activity compared to addition of the known fibrolytic enzyme alone.

Example 11

Rumen-simulating continuous cultures were used to examine the effects of combining a commercial fibrolytic enzyme supplement (FIBROZYME™; Alltech, Inc., Nicholasville, Ky.) and acetyl esterase-containing preparations on in vitro ruminal digestion processes. Rumen fluid was collected on day 0 from a fistulated steer receiving an alfalfa hay-based diet (Table 6). Rumen contents were filtered and used to inoculate rumen-simulating continuous cultures. The rumen-simulating continuous cultures were fed 20 g of fescue hay-based diet/d for 7 d. Treated cultures received a mixture of FIBROZYME (0.15 g/L) and liquid acetyl esterase (0.5 unit/L) preparation twice a day at each feeding while control cultures only received feed.

Digestibility of NDF and acid detergent fiber (ADF) were examined daily in enzyme treated and control cultures. Culture effluent subsamples and feed and inoculum samples were dried overnight in pre-weighed aluminum pans for DM determination as is known in the art. NDF and ADF on the feed, inoculum and dried effluents from each culture were determined using the Daisy[II] incubation system as described in Example 6. Digestibilities (DM, NDF and ADF) were estimated for each culture by calculating total DM, NDF and ADF input and output from total feed weight and total inoculum and effluent volumes.

Samples were collected daily from each culture for pH, VFA and ammonia concentration analyses. A pH meter was used to measure pH in the samples. Ammonia concentrations were analyzed by methods known in the art using L-glutamate dehydrogenase (Sigma Diagnostics Procedure 171-UV, Sigma Diagnostics, St. Louis, Mo.) in a centrifugal analyzer (Cobas Fara II; Roche Diagnostics Systems, Montclair, N.J.). Volatile fatty acid analyses were performed by gas chromatography, and hexose utilization was estimated stoichiometrically from VFA concentrations as described in Example 5.

The addition of FIBROZYME™ and acetyl esterase to rumen-simulating continuous cultures resulted in 9% greater total VFA concentrations and hexose utilization than in control cultures (Table 8). Concentrations of acetate, propionate and butyrate were 7.8, 10.8 and 11.7% greater in cultures receiving the exogenous enzyme supplement than in unsupplemented control cultures. The enzyme supplement also increased the amount of propionate produced relative to the amount of acetate produced as indicated by a lower acetate to propionate (A:P) ratio. In addition, ammonia concentrations were greater and pH was lower in enzyme supplemented cultures (Table 8).

The addition of FIBROZYME™ and acetyl esterase activities to ruminal-simulating continuous cultures increased DM digestibility of the fescue hay-based diet by 27% (Table 9). The digestibilities of the NDF and ADF fractions of feed tended to be greater in cultures receiving the exogenous enzyme supplements. The addition of the FIBROZYME™ and acetyl esterase containing supplement had no effects on the concentrations of total anaerobic, lactic acid-utilizing and cellulolytic bacteria (data not shown).

TABLE 9

Effects of adding FIBROZYME ™ and acetyl esterase on pH, VFA and ammonia concentrations and hexose utilization in rumen-simulating continuous cultures fed a fescue hay-based diet for 7d

| | Supplement[a] | | | |
|---|---|---|---|---|
| | None | Enzyme | SEM | P value[d] |
| VFA concentration (mmoles/L) | | | | |
| Total VFA | 112.7 | 122.8 | 2.19 | 0.001 |
| Acetate | 72.7 | 78.4 | 1.33 | 0.003 |
| Propionate | 21.2 | 23.5 | 0.43 | 0.001 |
| Butyrate | 12.8 | 14.3 | 0.32 | 0.006 |
| Isobutyrate | 2.3 | 2.5 | 0.06 | ns[e] |
| Valerate | 1.7 | 2.0 | 0.04 | 0.001 |
| Isovalerate | 2.0 | 2.3 | 0.05 | ns |
| A:P ratio | 3.47 | 3.37 | 0.017 | 0.001 |
| Net hexose utilization (mmoles/L) | 62.5 | 68.3 | 1.22 | 0.001 |
| $NH_3$ (mmoles/L) | 30.8 | 31.4 | 0.73 | 0.001 |
| pH | 6.92 | 6.86 | 0.010 | 0.001 |

[a]Values are triplicate means for d 1 through 7 (n = 21).
[b,c]Values in the same row with different superscripts differ (P < 0.05).
[d]Probability of equal means in enzyme supplemented and unsupplemented cultures.
[e]ns: not significant (P > 0.05).

TABLE 10

Effects of FIBROZYME ™ and acetyl esterase supplementation on in vitro DM, NDF and ADF digestibility in rumen-simulating continuous cultures fed a fescue hay-based diet for 7d

| In vitro digestibility (g) | Supplement[a] | | | |
|---|---|---|---|---|
| | None | Enzyme | SEM | P value[b] |
| DM | 47.4 | 60.2 | 3.32 | 0.052 |
| NDF | 52.1 | 56.5 | 1.84 | 0.161 |
| ADF | 24.7 | 26.8 | 0.91 | 0.177 |

[a]Mean values (n = 3).
[b]Probability of equal means in enzyme supplemented and unsupplemented cultures.

The addition of FIBROZYME™ or acetyl esterase activities to batch cultures of ruminal microorganisms enhanced the rate of in vitro digestion of a fescue hay-based diet as indicated by greater rates of gas production during incubation for 12 h. These observations support the hypothesis that some exogenous enzyme supplements have the ability to increase the rate of digestion during the initial period of fermentation.

Data from rumen-simulating continuous cultures shows that the combination of FIBROZYME™ and acetyl esterase activities effectively enhances ruminal digestion of a fescue hay-based diet in vitro. The addition of an exogenous enzyme supplement containing FIBROZYME™ and acetyl esterase activities increased in vitro VFA production, hexose utilization and DM digestibility from fescue hay without affecting the concentrations of total anaerobic, lactic acid-utilizing and cellulolytic bacteria. These observations support the hypothesis that exogenous enzyme effects on ruminal digestion occur by increasing the rate of digestion without increasing ruminal bacterial concentrations.

However, the FIBROZYME™-acetyl esterase combination also influenced microbial activity (but not relative concentrations) as indicated by increased propionate production relative to acetate production. Therefore, while not wishing to be bound by any particular theory, this particular enzyme supplement improves ruminant performance by increasing the digestion of plant materials in the diet and by shifting ruminal fermentation towards more energy efficient substrate utilization.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for enhancing plant fiber digestion in an animal, said method comprising feeding an effective amount of an acetyl esterase-containing composition to said animal, wherein said acetyl esterase is derived from Orpinomyces spp. KY, on deposit with the American Type Culture Collection as PTA-4235.

2. The method of claim 1, wherein the effective amount of the acetyl esterase-containing composition fed comprises 50 to about 5000 units of acetyl esterase per animal per day.

3. The method of claim 2, wherein the effective amount of the acetyl esterase-containing composition fed comprises 100 to about 2000 units of acetyl esterase per animal per day.

4. The method of claim 3, wherein the animal is a ruminant animal.

5. The method of claim 4, wherein the ruminant animal is a bovine animal.

6. The method of claim 5, wherein the ruminant animal is a lactating bovine animal.

7. The method of claim 1, wherein the acetyl esterase-containing composition administered to the ruminant animal contains no cellulase activity and no xylanase activity.

8. The method of claim 1, wherein the animal is an equine, porcine, ovine, caprine or avian species.

9. The method of claim 8, wherein the avian species is a species of poultry.

10. The method of claim 1, wherein the acetyl esterase-containing composition is fed to said mammal in an amount sufficient to provide enzymatic activity from about 1 to about 10 U/kg of digesta.

11. The method of claim 1, further comprising feeding an effective amount of a cellulase and xylanase-containing composition to said mammal.

12. The method of claim 11, wherein the acetyl esterase, cellulase, and xylanase are fed to said mammal in an amount sufficient to provide enzymatic activity of from about 1 to about 10 U of acetyl esterase/kg of digesta, from about 30,000 to about 120,000 U of cellulase/kg of digesta, and from about 2000 to about 5000 U of xylanase/kg of digesta.

13. The method of claim 12, wherein the acetyl esterase, cellulase, and xylanase are fed to a ruminant, equine, porcine or avian species.

* * * * *

UNITED STATES PATENT AND TRADEMARK OFFICE
CERTIFICATE OF CORRECTION

PATENT NO. : 6,750,051 B2
DATED : June 15, 2004
INVENTOR(S) : Tricárico et al.

It is certified that error appears in the above-identified patent and that said Letters Patent is hereby corrected as shown below:

Columns 9 and 10,
Table 2, line 1, 6th column, delete "2937.7" and replace with -- 37.7 --.

Column 10,
Line 29, delete "h" before "total".

Columns 13 and 14,
Table 4, propionate column, line 7, delete "6.9b$^b$" and replace with -- 6.9$^b$ --.

Column 20,
Lines 2, 7 and 9, delete "mammal" and replace with -- animal --.

Signed and Sealed this

Fourteenth Day of December, 2004

JON W. DUDAS
*Director of the United States Patent and Trademark Office*